US009366626B2

(12) United States Patent
Pastore et al.

(10) Patent No.: US 9,366,626 B2
(45) Date of Patent: Jun. 14, 2016

(54) METHOD AND APPARATUS FOR THE APPLICATION OF FORCE TO A SAMPLE FOR DETECTION USING AN ELECTROMECHANICAL MEANS

(71) Applicant: Thermo Scientific Portable Analytical Instruments Inc., Tewksbury, MA (US)

(72) Inventors: Timothy M. Pastore, Wakefield, MA (US); Kenneth J. Vachon, Jr., Holliston, MA (US); Brendon D. Tower, Weymouth, MA (US); Gregory H. Vander Rhodes, Melrose, MA (US); Aaron Sean Poynton, Joppa, MD (US)

(73) Assignee: Thermo Scientific Portable Instruments Inc., Tewksbury, MA (US)

( * ) Notice: Subject to any disclaimer, the term of this patent is extended or adjusted under 35 U.S.C. 154(b) by 122 days.

(21) Appl. No.: 13/922,827

(22) Filed: Jun. 20, 2013

(65) Prior Publication Data
US 2014/0374601 A1    Dec. 25, 2014

(51) Int. Cl.
*G01J 5/02*       (2006.01)
*G01N 21/552*  (2014.01)
*G02B 21/26*    (2006.01)
*G01J 3/02*       (2006.01)

(52) U.S. Cl.
CPC ............ *G01N 21/552* (2013.01); *G01J 3/0272* (2013.01); *G02B 21/26* (2013.01)

(58) Field of Classification Search
CPC ...... G01N 21/522; G02B 21/26; G01J 3/0272
See application file for complete search history.

(56) References Cited

U.S. PATENT DOCUMENTS

| 6,414,311 | B1 | 7/2002 | Wood et al. |
|---|---|---|---|
| 2003/0155511 | A1* | 8/2003 | Hisazumi et al. ........ 250/339.12 |
| 2009/0237647 | A1 | 9/2009 | Azimi et al. |
| 2012/0008196 | A1 | 1/2012 | Juette et al. |
| 2012/0262710 | A1 | 10/2012 | Aeschbach |

OTHER PUBLICATIONS

"The effects of varying force and contact on ATR spectra," Technical Note, Jan. 1, 2012, Retrieved from the Internet: URL:http://www.perkinelmer.co.uk/MCSResources/Images/44-135840TCH_010127_01_ATR.pdf [retrieved on Sep. 5, 2014].

* cited by examiner

*Primary Examiner* — David J Makiya
*Assistant Examiner* — Kenneth J Malkowski
(74) *Attorney, Agent, or Firm* — Ion C. Abraham

(57) ABSTRACT

The embodiments of the present invention are directed to applying intimate contact pressures to samples while undergoing ATR infrared interrogation. As a general mode of operation, after a solid sample is placed on the ATR element, a force actuator moves an anvil arm to apply a contact force to the sample against the ATR. Thereafter, when the scan is over, the user can see the result of the one or more scans. The force actuator may be a motor or a solenoid or other type of force actuator. The applied contact force may be a fixed force or may be a user-selectable force or may be automatically controlled through feedback from the spectrometer based on the spectroscopic signature of the sample material.

17 Claims, 7 Drawing Sheets

METHOD AND APPARATUS FOR THE APPLICATION OF FORCE TO A SAMPLE FOR DETECTION USING AN ELECTROMECHANICAL MEANS

This invention was made with Government support under Contract Number N00178-04-D-4143 awarded by Naval Explosive Ordnance Disposal Technology Division (NAVEODTECHDIV). The Government has certain rights in the invention.

BACKGROUND OF THE INVENTION

1. Field of the Invention

The present invention relates to spectroscopy and more specifically, the present invention relates to an ATR/FTIR spectroscopic system and method that can also automatically provide different contact pressures while providing timed delay capabilities as a beneficial feature.

2. Description of Related Art

Attenuated total reflectance (ATR) is an optical interrogation technique often used in conjunction with infrared spectroscopy (e.g., Fourier Transform Infrared (FTIR)), which enables samples to be examined directly in a solid, liquid or a gas state. In particular, ATR capitalizes on total internal reflected light produced at the interface of a configured internally reflecting element (IRE) and a coupled sample plane. In operation, a beam of light (e.g., infrared) is passed through the IRE crystal in such a way that it reflects at least once off of the internal surface in contact with the sample. This reflection forms an evanescent wave which extends into the sample, often up to about 2 microns, with the exact value being determined by the wavelength of light, the angle of incidence and the indices of refraction for the IRE crystal and the sample medium being interrogated. The reflected beam, which carries the spectral information of the sample, is thereafter interrogated for analysis via, for example, a single pixel, linear array or 2 dimensional array detector.

As generally alluded to above, the samples, primarily the solid samples to be interrogated using ATR as the investigation technique, can come in the form of many different shapes and sizes. In order to enable efficient optical coupling, a force must be applied to such samples with a configured stage mechanism that is designed to provide intimate contact with an optical component, such as a Diamond, Silicon, or Germanium (Ge) ATR element. Conventional stages include pressure mechanisms that include mechanical screws, levers, slides, and actuators that are designed to apply compressive forces on a given sample.

However, while a pressure mechanism is required to compress the sample tightly against the desired ATR element surface to enable intimate contact, it is to be noted that in some cases, applying such force with speedily and repeatably with conventional means can be difficult for the person operating the instrument.

Accordingly, the present invention is directed to providing a compact ATR/FTIR optical instrument that is configured to provide different contact pressures to preferred samples as part of the operation. In particular, the present invention includes controlling the contact force being applied to any material and with an additional novel feature of a time delay (interval) means to allow the user to be positioned at a remote location during operation.

SUMMARY OF THE INVENTION

An aspect of the present application is to provide a handheld internal reflection apparatus that includes: a handheld enclosure; an internally reflective element disposed in the handheld enclosure and also configured to provide a sample contact surface external to the handheld enclosure; an optical assembly contained within the handheld enclosure, the optical assembly further comprising a radiation source and a radiation detector, the source being configured to direct radiation towards the sample contact surface and the detector being configured to detect the source radiation optically interacting with the sample contact surface; a sample contact arm; a force actuator coupled to the sample contact arm; and a processor also configured within the handheld enclosure and electronically coupled to the force actuator, the radiation source, and the radiation detector; wherein the processor directs the force actuator with a controlled contact force as applied to a sample disposed between the sample contact arm and the sample contact surface, wherein after the controlled contact force is met, the electronic processor analyzes the sample information received by the radiation detector.

Another aspect of the present application is to provide a handheld internal reflection method that includes: moving a sample contact arm configured with an ATR handheld instrument to a desired position over a sample; axially moving the sample contact arm using a processor controlled force actuator, wherein the sample contact arm movement provides a controlled contact force to be applied to the sample and a measuring surface of an internally reflective element; and stopping movement of the sample contact arm after the controlled contact force with the sample and the measuring surface of the internally reflective element meets predefined force settings configured within the ATR handheld instrument or provides a reasonable feedback spectroscopic signal of the sample material.

Accordingly, the embodiments disclosed herein provide for intimate contact pressures to be applied to a variety of solid samples in a controlled manner to enable ATR infrared (FTIR) interrogation. In particular, after a sample is placed on the ATR element, a force actuator moves an anvil arm to apply a contact force to the sample against the ATR after the user exits the immediate area via a timed countdown (scan "delay" function) operation. Thereafter, when the scan is over, the user can approach the instrument and see the result of the one or more scans.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

Figure 1:
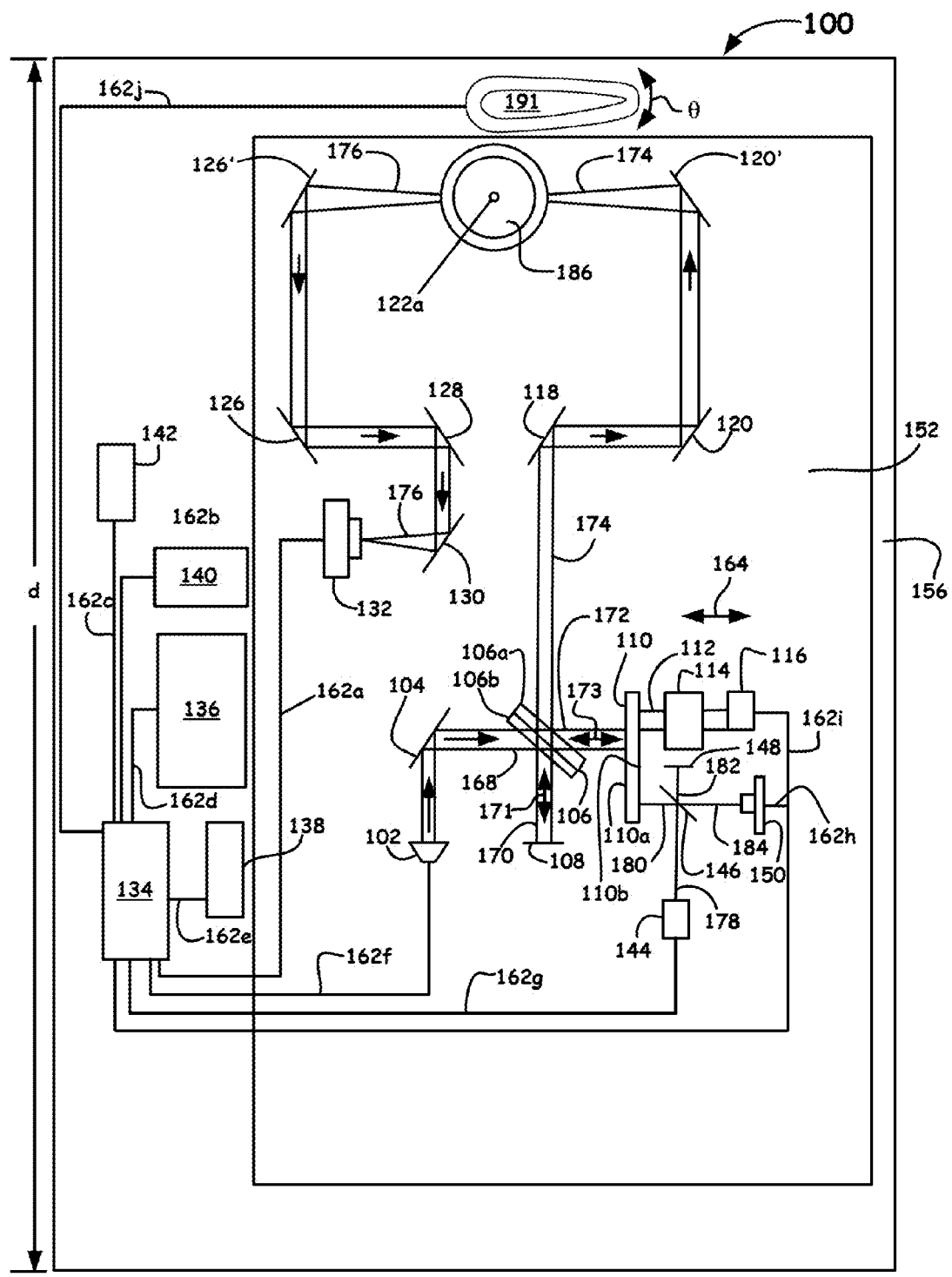
FIG. 1 shows a schematic representation of an ATR example embodiment, as disclosed herein.

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it will be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

GENERAL DESCRIPTION

In Fourier Transform Infrared (FTIR) spectroscopy, the unknown substance is illuminated with a broad-spectrum of infrared light, which can be absorbed by the sample of interest. The illumination via a source known to those skilled in the art is often in the wavelength range from about 0.7 microns up to 25 microns. The light intensity as a function of wavelength is measured before and after interacting with the sample, and the absorbance caused by the sample is calculated. Light is absorbed in varying amounts by the sample at particular frequencies corresponding to the vibrational frequencies of the bonds of the molecules in the sample. Since the bonds for every molecule are different, the FTIR absorption spectrum for every molecule is also different. Thus, a spectral "fingerprint" can be generated by recording the absorbance of light as a function of wavelength.

Most substances absorb this infrared light very readily, and if all of the light is absorbed, there will be no light reaching the detector to be analyzed. Therefore, care must be taken in how the light is delivered to and collected from the sample. The most user-friendly method for field use is called attenuated total reflection (ATR), and uses an internally reflecting element having a high index of refraction, such as diamond or Germanium, to send light into just the first few microns of the sample before returning back to provide the optical information of the sample.

With typical ATR/FTIR instruments, the conventional pressure arrangement uses drive screws, levers, and wedges to create pressure on the materials and requires the user to manually move the mechanism. Such conventional manual (e.g., knob driven) movement of the mechanism, however, tend to be large and unwieldy, and are also difficult to manipulate in ways that apply contact force repeatably or according to desired attributes such as a desired spectroscopy signature.

Therefore, to address the issues described above, the disclosed embodiments herein are designed to not only compress any solid material configured for ATR infrared (FTIR) interrogation by the instruments herein, but to also compress any of the materials being measured in a manner that is repeatable and that is amenable to controls such as force feedback or spectral signature feedback. The general mode of operation of the instrument(s) described herein is as follows: after a solid sample is placed on the ATR element (i.e., a platform), an actuator moves an anvil to apply a force to the sample against the ATR. The user may exit the immediate area via a timed ("delay" interval function) operation. The actuator may be a motor or a solenoid or other type of force actuator. The applied force may be a fixed force or may be a user-selectable force or may be automatically controlled through feedback from the spectrometer based on the spectroscopic signature of the sample material.

With respect specifically to the aforementioned time "delay" operation, such a mode provides a deemed novel safety component in measuring samples in an ATR instrument. In particular, the scan delay feature enables safe "user" operational distances while providing controlled (e.g., programmed) contact pressure(s) to the sample undergoing ATR/FTIR interrogation, as disclosed herein. Such an arrangement, as one example, allows a user to provide a sample material to the instrument described herein and set a countdown timer. While the timer is counting down, the user can get to a safe distance at which time the instrument can begin the infra-red (e.g., FTIR) interrogation of the sample once a particular contact pressure is enabled. Thereafter, when the scan is over, the user can approach the instrument and see the result of the one or more scans.

It is to be stressed again that while the configurations disclosed herein are beneficial in interrogating energetic or otherwise pressure sensitive materials, it is also to be appreciated that the configurations disclosed herein are not strictly limited to just energetic or pressure sensitive materials. In particular, the configurations herein can also address any solid or liquid material capable of ATR analysis, as enabled by the design parameters of the present application.

As an additional alternative embodiment, the configuration(s) herein can also include a scan timeout function. Such an option for the user entails the removal of pressure from the sample in a timed operation while the operator is still in a remote location. The reasoning for choosing this option is because, similar to applying pressure to suspect materials, the removal of pressure can also cause deleterious friction and breaking of, for example, crystalline explosive material.

SPECIFIC DESCRIPTION

Many applications exist for portable measurement devices, including field identification of unknown substances by law enforcement and security personnel in addition to the detection of prohibited substances at airports and in other secure and/or public locations. To be useful in a variety of situations, it is beneficial to be portable via a handheld form factor instrument that also provides rapid and accurate results.

The measurement instruments and methods disclosed herein thus provide for such a handheld form factor that enables not only ease of transport but with a desired accuracy in results. In particular, the embodiments disclosed herein are configured in compact packages that enable intimate various contact pressures between a sample of interest and an ATR optical element positioned in the instrument that collectively enables FTIR investigation of suspected materials. The ATR high index of refraction optical element as configured in the instrument, such as a Diamond or Germanium, or a Silicon reflective element, operates by ensuring that non-absorbed incident radiation is directed to a detector after undergoing total internal reflection via the configuration of the element. As a result, reflected radiation is coupled with high efficiency to the detector, ensuring sensitive operation of the measurement devices.

Samples of interest can be identified based on the reflected radiation that is measured by the detector. The reflected radiation can be used to derive infrared absorption information corresponding to the sample, and the sample can be identified by comparing the infrared absorption information to reference information for the sample that is stored in the measurement device. In addition to the identity of the sample, the measurement device can provide one or more metrics (e.g., numerical results) that indicate how closely the infrared absorption information matches the reference information. Furthermore, the measurement device can compare the identity of the sample of interest to a list of prohibited substances, also stored within the measurement device, to determine whether particular precautions should be taken in handling the substance, and whether additional actions by security personnel, for example, are warranted.

General System Configuration

Turning to the drawings, FIG. 1 is provided to illustrate to the reader the overall workings of an ATR/IR instrument described herein, as generally referenced by the numeral 100. A similar system can also be found in U.S. Pat. No. 7,928,391, entitled: "Handheld Infrared and Raman Measurement Devices and Methods," to Azimi et al. and assigned to the assignees of the present application, the disclosure of which is hereby incorporated by reference in its entirety.

With respect to the present application, instrument 100 shows assorted optical components mounted on an assembly support 152 within an enclosure 156. Importantly, FIG. 1 also shows an ATR platform 186 and a moveable (rotationally and vertically) sample contact arm (hereinafter anvil arm 191 for simplicity of discussion), i.e., preferably a motorized anvil arm, mounted external to the enclosure 156, to be discussed in detail later below. It is to be noted that while the instrument shown in FIG. 1 can be externally powered, the complete unit (i.e., instrument 100) can often be powered by a battery, most often a rechargeable battery as known to those skilled in the art for complete portability.

The assorted optical components of FIG. 1 can include: radiation sources 102 and 144; mirrors 104, 108, 110, 148, 118, 120, 120', 126, 126', 128, and 130; beamsplitters 106 and 146; detectors 132 and 150; and an ATR element (e.g., a prism, (not shown)) configured cooperatively with ATR platform 186. It is to be noted that while FIG. 1 shows mirrors 104, 108, 110, 148, 118, 120, 120', 126, 126', 128, and 130 of a certain number and as generally planar in design, it is to be noted that other optical elements of any number, to include refractive optical elements (e.g., lenses) as well as non-planar reflective elements can also be configured with other predetermined curvatures to provide the optical paths shown in FIG. 1. For example, such elements can be configured with concave, convex, parabolic, elliptical curvatures or any general surface needed to provide proper beam construction along any part of the beam paths as directed within instrument 100.

Instrument 100 also includes a shaft 112, a bushing 114, and an actuator 116 coupled to mirror 110, and an electronic processor 134, an electronic display (e.g., including a flat panel display element such as a liquid crystal display element, an organic light-emitting diode display element, an electrophoretic display element, or another type of display element capable of touch-screen operation), an input device 138, a storage unit 140, and a communication interface 142. Also shown in FIG. 1 is an electronic processor 134 that is in electrical communication with detector 132, storage unit 140, communication interface 142, display 136, input device 138, radiation sources 102 and 144, detector 150, moveable anvil arm 191, and actuator 116, respectively, via communication lines 162a-j.

Instrument 100, if configured for use as a Fourier transform infrared (FTIR) spectrometer during operation, provides radiation 168 via radiation source 102, which can be removable for ease of replacement, under the control of processor 134. Radiation 168 is directed by mirror 104 to be incident on beamsplitter 106, configured as a beamsplitting optical element 106a and a phase compensating plate 106b to enable the received radiation 168 to be divided into two beams. Using such a configuration enables a Michelson-type of interferometer to be formed wherein a first beam 170 reflects from a surface of beamsplitter 106, propagates along a beam path which is parallel to arrow 171, and is incident on fixed mirror 108. Fixed mirror 108 thereafter reflects first beam 170 in an opposite direction so as to be now be directed towards beamsplitter 106. A second beam 172 is transmitted through beamsplitter 106 and propagates along a beam path which is parallel to double arrow 173. Second beam 172 is incident on a first surface 110a of movable mirror 110 so that upon reflection is also directed towards beamsplitter 106.

First and second beams 170 and 172 are thus combined by the configuration of beamsplitter 106 and associated optics, which spatially overlaps the beams to form a beam of modulated infrared radiation beam 174 (by way of operation of the configured Michelson interferometer) and is directed towards mirror 118. Thereafter, mirrors 118, 120, 120' direct modulated infrared radiation beam 174 to an ATR optical element (not shown in detail but ATR surface face 122a is illustrated). Once inside the ATR optical element (often configured as a prism), beam of modulated infrared light 174 is directed to a surface face 122a (shown as a plan view in FIG. 1) of the ATR optical element (e.g. prism). Surface face 122a of the ATR optical element is positioned such that it contacts a sample of interest (not shown), often a sample having irregularities in surface construction (e.g., a powder). When modulated infrared light 174 is incident on surface face 122a, a portion of the radiation of modulated infrared light 174 is coupled into the sample material (not shown) through surface 122a via a desired evanescent wave effect, as known to those of ordinary skill in the art. As part of the effect, the sample desirably absorbs a portion of modulated infrared light 174 that is indicative of the structure and thus the properties of the sample material.

The total internal reflected portion of modulated infrared light 174, denoted as reflected beam 176, now includes a reduced amount of modulated radiation not absorbed by the sample (not shown), of which is also indicative of the properties of the sample (not shown). As a result of the configuration, reflected beam 176 is directed through a desired surface of the ATR optical element and is thereafter directed by, for example, mirrors 126', 126, 128, and 130 in order to be interrogated by instrument 100 via detection by detector 132. In particular, under the control of processor 134, detector 132 can be configured to measure one or more properties of a sample (not shown) based on the reflected radiation in beam 176.

As stated above, the configured mirrors 108 and 110 together with beamsplitter 106 beneficially form a Michelson interferometer. In operation, by translating mirror 110 as indicated by double-arrow 164 prior to each measurement, the plurality of measurements of the radiation in reflected beam 176 form an interferogram that includes information, such as sample absorption information. Processor 134 can be configured to apply one or more mathematical transformations (e.g., a Fourier transform) to the interferogram to obtain the sample absorption information. For example, processor 134 can be configured to transform the interferogram measurements from a first domain (such as time or a spatial dimension) to a second domain (such as frequency) that is conjugate to the first domain.

To provide movement of mirror 110, the element itself is coupled to shaft 112, bushing 114, and actuator 116. The shaft 112 moves freely within bushing 114 and a viscous fluid is often disposed between shaft 112 and bushing 114 to permit relative motion between the two. Thus, mirror 110 moves when actuator 116 receives control signals from processor 134 via communication line 162*i*. Actuator 116 initiates movement of shaft 112 in a direction parallel to arrow 164 and mirror 110 moves in concert with shaft 112. Bushing 114 provides support for shaft 112, preventing wobble of shaft 112 during translation. However, bushing 114 and shaft 112 are effectively mechanically decoupled from one another by the fluid disposed between them; and thus mechanical disturbances, such as vibrations, are coupled poorly between shaft 112 and bushing 114. As a result, the alignment of the resultant Michelson interferometer remains relatively undisturbed even when mechanical perturbations, such as vibrations, are present in other portions of instrument 100.

To measure the position of mirror 110, instrument 100 provides an assembly that includes radiation source 144, beamsplitter 146, mirror 148, and detector 150. These components are arranged to form a second Michelson interferometer. During a mirror position measurement of operation, radiation source 144 (e.g., a monochromatic emission source (laser)) receives a control signal from processor 134 via communication line 162*g*, and generates a radiation beam 178. As an example of a desired source, radiation source 144 can be a configured vertical cavity surface-emitting laser (VCSEL) that generates radiation having a central wavelength of 850 nm. However, it is to be understood that source 144 can also include a wide variety of other sources, such as, laser diodes, light-emitting diodes, etc., capable of having radiation between 400 nm up to about 1200 nm.

Turning back to the discussion for FIG. 1, beam 178 is incident on beamsplitter 146, which separates radiation beam 178 into a first beam 180 and a second beam 182. First beam 180 reflects from the surface of beamsplitter 146 and is incident on a second surface 110*b* of mirror 110. Second surface 110*b* is positioned opposite first surface 110*a* of mirror 110. First beam 180 reflects from surface 110*b* and returns to beamsplitter 146.

Second beam 182 is transmitted through beamsplitter 146, reflected by mirror 148, and returned to beamsplitter 146. Beamsplitter 146 combines (e.g., spatially overlaps) reflected beams 180 and 182, and the spatially overlapped beam 184 is directed to detector 150. Detector 150 receives control signals from processor 134 via communication line 162*h*, and is configured to measure an intensity of combined beam 184. Combination beam 184 provides an interference pattern that contains desired optical position information. Thus, monitoring beam 184 enables the position (and speed and tilt, if desired), of mirror 110 to be precisely determined by counting the peaks and valleys in the amplitude of beam 184.

As a beneficial aspect of the present application, absorption information can be compared by processor 134 to reference information (e.g., reference absorption information) stored in storage unit 140 to determine an identity of an unknown sample (not shown). For example, processor 134, after a Fourier transform has been applied to the received reflected beam 176, can determine whether the absorption information for the sample matches any one or more of a plurality of sets of reference absorption information for a variety of substances that are stored as database records in storage unit 140 or even from a database remotely located via wireless communication. If a match is found (e.g., the sample absorption information and the reference information for a particular substance agree sufficiently), then sample 190 is considered to be identified by processor 134. Processor 134 can send an electronic signal to display 136 along communication line 162*d* that indicates to a system operator that identification of sample 190 was successful, and provides the name of the identified substance. The signal can also indicate to the system operator how closely the sample absorption information and the reference information agree. For example, numeric values of one or more metrics can be provided which indicate the extent of correspondence between the sample absorption information and the reference information on a numerical scale.

If a match between the sample absorption information and the reference information is not found by processor 134, the processor can send an electronic signal to display 136 that indicates to the system operator that sample 190 was not successfully identified, or that efficient optical coupling between the ATR surface face 122*a* was not provided because of insufficient force applied by moveable anvil arm 191. The electronic signal can include, in some embodiments, a prompt to the system operator to repeat the sample absorption measurements or perhaps choose an operation that can provide ample anvil arm 191 contact force.

If identification of sample 190 is successful, processor 134 can be configured to compare the identity of sample 190 against one or more lists of prohibited substances stored in storage unit 140. If sample 190 appears on a list as a prohibited substance, processor 134 can alert the system operator that a prohibited substance has been detected. The alert can include a warning message provided on display 136 and/or a colored region (e.g., a red-colored region) on display 136. Processor 134 can also be configured to sound an audio alarm via a speaker to alert the system operator.

Instrument 100 also includes communication interface 142, which receives and transmits signals from/to processor 134 via communication line 162*c*. Communication interface 142 includes a wireless transmitter/receiver unit that is configured to transmit signals from processor 134 to other devices, and to receive signals from other devices and communicate the received signals to processor 134. Typically, for example, communication interface 142 permits processor 134 to communicate with other devices via a wireless network that includes multiple devices connected to the network, and/or via a direct connection to another device. Processor 134 can establish a secure connection (e.g., an encrypted connection) to one or more devices to ensure that signals can only be transmitted and received by devices that are approved for use on the network.

Processor 134 communicates with a central computer system to update the database of reference information stored in storage unit 140. Processor 134 is configured to periodically contact the central computer system to receive updated reference information, and processor 134 can also receive automatic updates that are delivered by the central computer system. The updated reference information can include reference absorption information, for example, and can also include one or more new or updated lists of prohibited substances.

Processor 134 can also communicate with other measurement devices to broadcast alert messages when certain substances, such as substances that appear on a list of prohibited substances, are identified, for example. Alert messages can also be broadcast to one or more central computer systems. Alert information, including the identity of the substance, the location at which the substance was identified, the quantity of the substance, and other information, can also be recorded and broadcast to other measurement devices and computer systems.

In some embodiments, instrument 100 can be connected to other devices over other types of networks, including isolated local area networks and/or cellular telephone networks. The connection can also be a wireless connection or a physical coupling.

As non-limiting examples of a wireless connection, such an arrangement can include commercial wireless interfaces, such as but not limited to, radio waves (WiFi), infrared (IrDA), or microwave technologies that also allow integration into available portable personal devices, such as, but not limited to, cell phones, pagers, personal identification cards, laptops, etc. The wireless communication can thus provide signals, including alert messages if detected, to be transmitted from processor 134 to such network-enabled devices that can alert personnel in the event that particular suspect are detected by instrument 100.

The wireless network can, for example, optionally include an open standard for short-range transmission of digital voice and data between the aforementioned portable but also fixed devices that support point-to-point and multipoint applications. For example, communication interface 142, as shown in FIG. 1, can be configured with Bluetooth, which operates in a globally available frequency band (i.e., 2.4 GHz), ensuring communication compatibility worldwide, or Electronic and Electrical Engineers IEEE technologies (e.g., (IEEE) 802.11a or IEEE 802.11b) as the communication means based on its present common use in both business and home environments. Such popular technologies enable users' high-speed access to networks and the Internet while roaming throughout an area. Moreover, other protocols for wireless, such as IEEE 802.15, IEEE 802.16, GPS, 3G and others, may also be configured as a protocol for the communication standard of the present embodiments disclosed herein.

With respect to physical wired coupling, the coupling can be by way of a dedicated coupling I/O means, such as a USB port (not shown) to provide, for example, operational data (feedback) via the embedded software (e.g., firmware) or instructions received from processor 134 for programmatic control instruction.

Typically, the desired input device 138 includes a control panel that enables a system operator to set configuration options and change operating parameters of instrument 100. In some embodiments, instrument 100 can also include an internet-based configuration interface that enables remote adjustment of configuration options and operating parameters. The interface can be accessible via a web browser, for example, over a secured or insecure network connection. The internet-based configuration interface permits remote updating of instrument 100 by a central computer system or another device, ensuring that all measurement devices that are operated in a particular location or for a particular purpose have similar configurations. The internet-based interface can also enable reporting of device configurations to a central computer system, for example, and can enable tracking of the location of one or more measurement devices.

Turning to the radiation source for the instrument 100, radiation source 102, which is often configured as a replaceable component, includes a broadband radiation source configured to provide infrared radiation so that instrument 100 can be operated as an infrared spectrometer. Typically, for example, the infrared radiation provided by source 102 includes a distribution of wavelengths, with a center wavelength of the distribution of about 10 microns. In general, radiation source 102 can include a variety of sources known to those skilled in the art, including a heated infrared source chosen from any customized or conventional known source utilized in the field, such as, but not limited to, a wire, metal or ceramic element that is heated to emit a continuous band of optical radiation.

Typically, a characteristic temperature of the quasi-blackbody distribution of wavelengths of the radiation provided by source 102 can be between 700° C. up to 2000° C. and with emissivity between 0.4 and 0.95. It is to be noted, however, that the temperature of radiation 168 can be varied (e.g., via a control signal from processor 134 transmitted along communication line 162*f*) according to the particular sample 190 and the sensitivity of detector 132. Suitable broadband detectors 132 to generate an electronic signal include a pyroelectric detector or other detection elements, such as, bolometers, lead salt detectors, and mercury cadmium telluride detectors. a photodiode, avalanche photodiode, linear or 2D array or any detection element that can generate an electronic signal when subjected to an intensity of either beam 176 or beam 184. Photodiodes, avalanche photodiodes, quadrant photodiodes, or 2D arrays are desirable with respect to detector 150, with the multi-element detectors being used with dynamic alignment.

ATR/Prism Assembly Discussion

Figure 2A:
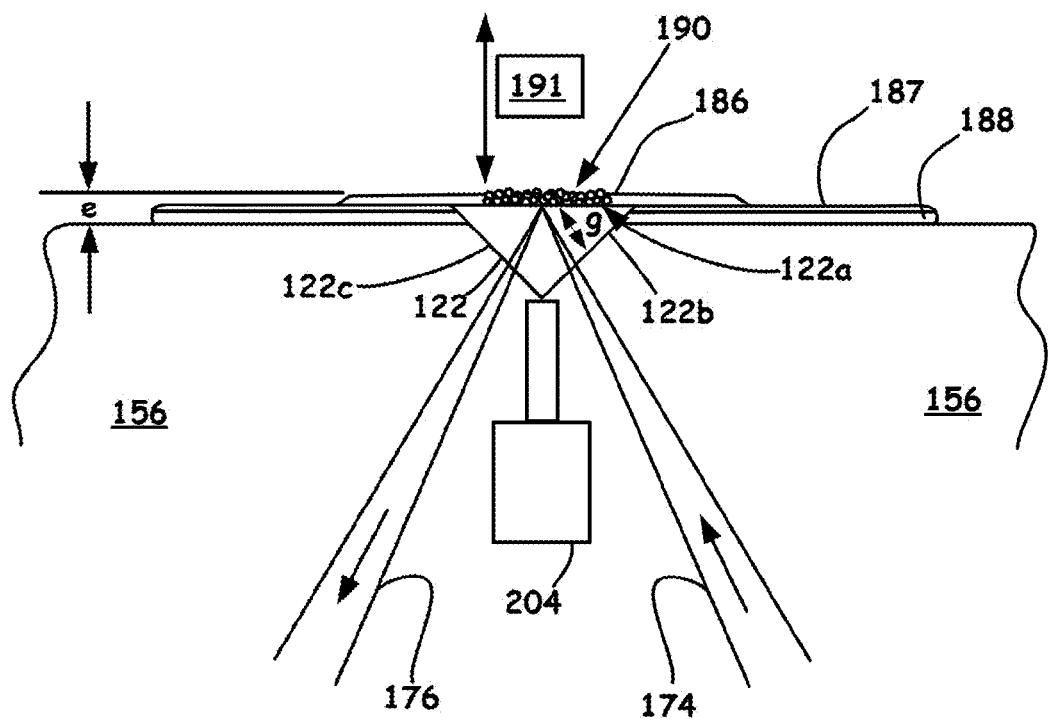
FIG. 2A shows an example diagram of a sample platform and ATR assembly.

FIG. 2A shows an enlarged general view of the ATR platform 186, 187, etc., and reflective element (hereinafter prism 122). Prism 122 includes a surface 122*a* positioned to contact sample 190 (e.g., shown as a powder (denoted as circles)), which can be a solid or a liquid desired to be measured using ATR principles but of which optionally may require safety measures while performing measurements on such materials, as described herein. Radiation from a source 102 configured within instrument 100, as described above, enters prism 122 through surface 122*b*, and leaves prism 122 through surface 122*c*.

An edge of prism 122 opposite to surface 122*a* is also but not necessarily supported from below by a prism base 204. A coating (not shown), such as a metal (e.g., gold), is also often applied to prism 122 to enable stable coupling to the top of configured surface 156 of instrument 100 to also provide support to prism 122 from above. Support provided by surface 156 and base 204 allows prism 122 to withstand significant applied forces during operation without being displaced from its mounting position.

As a general principle of operation of the instrument, after a solid unknown material 190 to be examined is placed on the attenuated total reflectance (ATR) element, i.e., surface face 122*a*, as also shown in FIG. 1, a sample contact actuator (e.g., an anvil actuator) to be disclosed herein applies a desired contact force to the sample material against the ATR surface face 122*a*. The actuator can, for example, be a motor (e.g., a DC motor) or a solenoid, an electromagnetic solenoid, or any type of force actuator (e.g., piezo-electric driven mechanism, linear motors, pneumatic or hydraulic actuators, etc.) that can be moved in a controlled manner to provide known or desired controlled compressive forces. Such actuators can also include cam or scissor jack configurations and if configured as a solenoid, such a solenoid can be, for example, a rotary solenoid that drives a pressure mechanism. The applied contact force using such actuators, while possibly being a fixed force or even a user-selectable force, more often can be automatically controlled through feedback, as previously discussed, from the spectrometer based on the spectrometer signature of the sample.

During operation, a system operator can motor control vertical movement of anvil arm 191 in a safe manner, as to be discussed below. Angular position θ of anvil arm 191, while capable of also being motor driven is more often manually provided by the user prior to operation of the instrument 100 for measurement(s). Thus, upon the sample being disposed on platform 186, and the sample contact arm (e.g., anvil arm 191) thereafter raised and rotated into position, a known or controlled compressive force of the sample material with prism 122 (e.g., surface face 122*a*) is provided automatically by the anvil actuator (not shown). Such a manipulation provides intimate contact between surface face 122*a* and sample material 190 to enable efficient coupling of the evanescent wave and improve a signal-to-noise ratio in measurements of reflected radiation beam 176. Support base 204 and surface 156 ensure that prism 122 remains in the same position within enclosure 156 during operation.

Figure 2B:
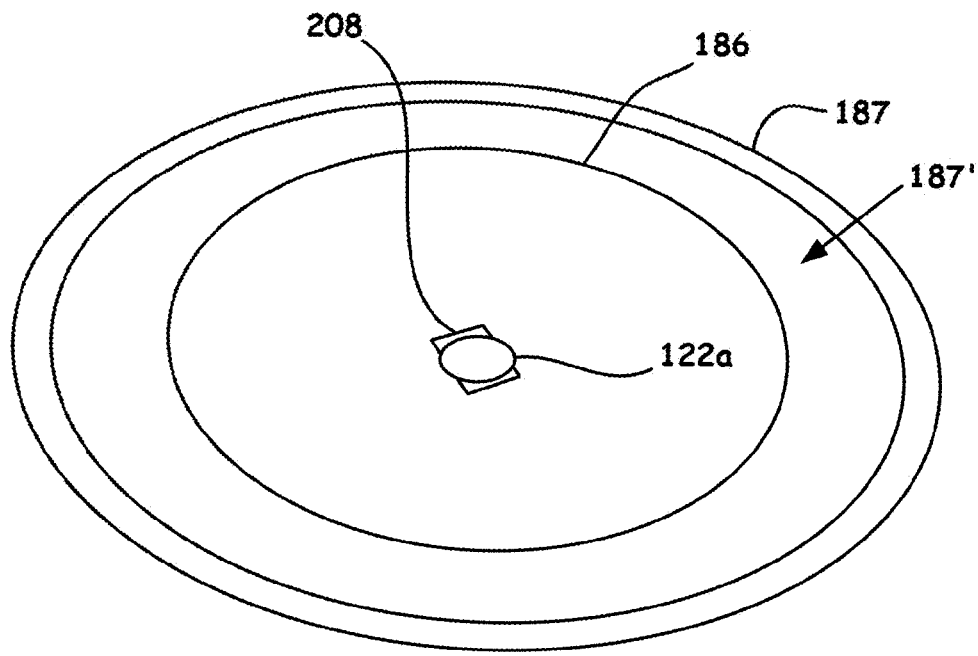
FIG. 2B shows an example isometric view of a platform and ATR surface that provides an aperture.

It is to be noted that ATR platform 186 extends outward for a distance e from surface 156. Generally, e can be between about 0.5 mm up to about 1.0 mm in height. However, it is not required that the ATR platform 186 extends outward from surface 156 at all. Platform 186 permits contact between sample 190 and surface 122*a* of prism 122 via a preferable planar surface configuration that results in an opening (not shown in detail) in platform 186 to surface face 122*a*. However, it is to be noted that while a planar surface configuration for platform 186 is preferred, other surfaces, e.g., curved concave surfaces, can also be implemented to enable receiving materials for ATR optical investigation, as configured with other aspects of the present application. An integral part of platform 186 is an extended section 187 that is configured with a moat-like configuration (187', as shown in FIG. 2B) designed with a curvature so as to catch any material that spills over from platform 186. A liquid-proof and often hermetic seal 188 is coupled to the platform (186 and 187) and surface. It is to be noted that prism 122 is mechanically coupled to the optical engine 152 but isolated from the housing 156 of instrument 100 to prevent the transmission of large-amplitude mechanical perturbations.

FIG. 2B shows an isometric perspective of the platform (186 and 187) that is not of the same scale as shown in FIG. 2A but gives the reader a better perspective of the ATR hardware platform 186, 187, and prism face 122*a* aperture arrangement. The reader should note that surface 187' is indicated generally but that such a surfaces can be configured with any curvature, such as, but not limited to, beveled, grooves, funnel shapes, etc., to contain overspill of a sample 190 adequately.

In the example view of FIG. 2B, surface 122*a* of prism 122 also shows a substantially circular cross-sectional shape. In general, however, prism 122 can also have a variety of different cross-sectional shapes, including ellipsoidal, rectangular, triangular, square, and irregular. In addition, surface 122*a* of prism 122, which is generally shown to be substantially planar, can also be arranged to protrude or perhaps be domed in the embodiment shown in FIG. 2B, and can be configured with a maximum dimension of between 0.5 mm and up to preferably 10 mm. With respect to the beam paths within the prism 122 shown in FIG. 2A, due to the symmetric arrangement of beams 174 and 176 with respect to prism 122, a total path length of the radiation in prism 122 is 2 g. In example embodiments, the total path length can be about 0.5 mm up to about 10 mm. It is also to be noted that FIG. 2B can often provide spacing 208 for a solder joint for secure placement of prism 122.

Anvil Configuration(s) and "Force" Mechanism(s)

As described throughout the present application, the example embodiments herein are beneficially directed to a compact ATR/FTIR optical instrument (i.e., handheld) that can automatically and/or manually provide movement to enable different intimate contact pressures to materials and the ATR optical element. Thus, as part of the novelty of the present application, instrument 100, as shown in FIG. 1, most often includes an embodiment of a moveable (e.g., motorized) ATR anvil arm 191 capable of being vertically and rotationally positioned via processor 134 along communication line 162*j*. Using such an arrangement enables the aforementioned intimate contact pressures and thus efficient coupling between the ATR element and an unknown sample.

However, while motorized automatic control is preferred, it is to be also noted that the embodiments herein can also include manual operation when and where desired. For example, a manually actuated anvil arm 191 can be configured as a parallel shaft-based system that uses an offset knob (not shown) protruding from the housing and capable of being coupled with an internal gear set that connects the knob to a screw mechanism that translates the anvil arm 191 up and down. Angular positioning θ can also be controlled automatically or manually. Another feature often utilized for the enclosure 156 is a recessed area 198 (shown in FIG. 3A and FIG. 3B to be discussed below) that is configured for the anvil arm 191 to reside and minimize protrusions that can hamper maneuverability of instrument 100. Moreover, the recessed area 198 enables clearance for a user, even a multi-gloved user, to also raise the anvil post 194 manually as an additional embodiment, and thus thereafter angular position anvil arm 191 over θ (e.g., up to about 90 degrees) over the sample platform 186 (see FIG. 3B) prior to operation of instrument 100.

Figure 3A:
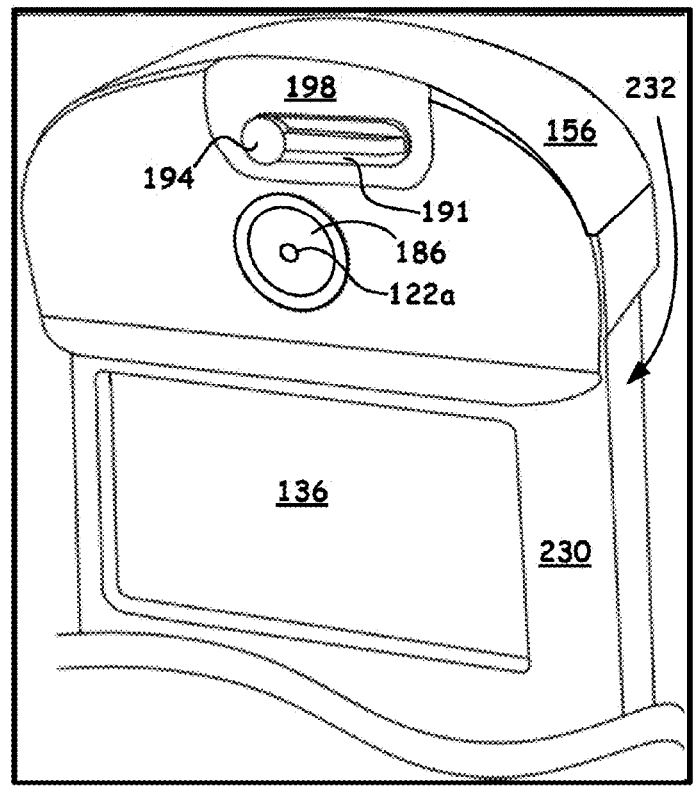
FIG. 3A shows an example isometric cutaway perspective of an ATR handheld instrument with the anvil arm disposed in a recessed area.
Figure 3B:
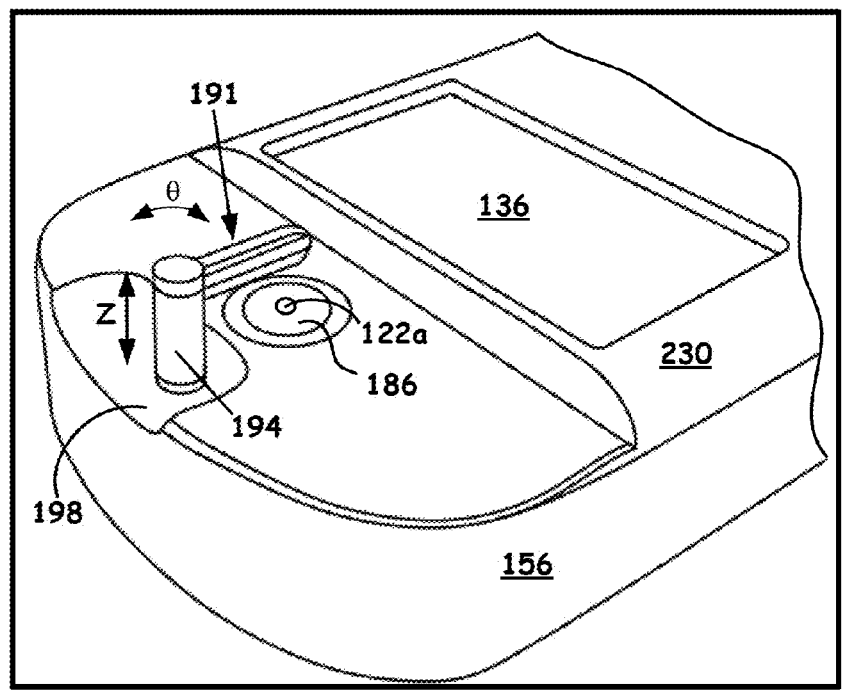
FIG. 3B shows an example isometric cutaway perspective of an ATR handheld instrument with the anvil arm angularly and vertically positioned as part of the operational capability of the instrument.

Thus, FIG. 3A and FIG. 3B show isometric cutaway perspectives of an enclosed instrument 100 of FIG. 1 to give the reader a better understanding of the present embodiments. In particular, FIG. 3A shows an example enclosure 156 with some but not all of the aforementioned elements of instrument 100, such as, display 136, ATR platform 186 and prism surface face 122*a*. FIG. 3A also shows a designed non-limiting example anvil arm 191 coupled to an anvil post 194 that can be driven by a desired force mechanism, i.e., actuator (not shown) up (Z as shown in FIG. 3A) for clearance of enclosure 156, angularly moved θ (as shown in FIG. 3B) via a motorized internal gear set, and thereafter down for vertical compression of a sample material, as discussed above.

FIG. 3B thus shows another isometric cutaway of enclosed instrument 100 and the recessed clearance 198 with the anvil arm 191 raised to a height Z and angularly θ moved to a position over, in particular, surface face 122a so as to be positioned for operation of the instrument, e.g., for scanning of a sample material. In contradistinction, the position for cleaning of anvil arm 191 is about 180 degrees (θ) rotation from what is shown in FIG. 3B. To provide robustness of the anvil arm 191 and surrounding parts, such elements can also be anodized, polished metal, or coated by, for example, physical vapor deposition for additional hardness.

Beneficial aspects of having not only recessed portions 198 for anvil arm 191 but even more so having a motorized force mechanism to translate anvil arm 191 include: a smaller form factor (no knob protrusions and less space inside enclosure 156, lighter by almost a factor of two, fewer moving parts (no telescope, clutch-thus enhancing reliability), fewer penetrations through housing (reduces leaks), easier to clean (fewer places for trapped debris), fewer operator touches, keeps user hands away from potentially dangerous sample(s), less chance of operator error (because of controlled contact pressure(s)), fewer catch points, and scan delay (to be discussed in detail below).

The enclosure 156, as generally noted in FIG. 3A and FIG. 3B, is desirably configured with a handheld form factor, so that instrument 100 functions as a handheld infrared spectrometer, and in particular, as a handheld Fourier transform infrared spectrometer. In some embodiments, enclosure 156 can include regions of narrowed width 232 that are positioned and dimensioned to fit the hand of a system operator, so as to facilitate operation of device 100 as a handheld device. In some embodiments, enclosure 156 can also include one or more shock-absorbing external protrusions 230, as generally indicated in FIG. 3A and FIG. 3B. The shock-absorbing external protrusions 230 can be formed (e.g., molded) from a viscoelastic material such as rubber, for example, and are most often configured to reduce or eliminate the transmission of mechanical vibrations to the components within enclosure 156, and generally to protect the components of instrument 100 as well. With respect to dimensional aspects, the embodiments herein are surprisingly even smaller and lighter than previous versions provided by the assignee of the present application, such as the designs disclosed in aforementioned incorporated by reference U.S. Pat. No. 7,928,391. As an example, typical maximum dimensions d, as denoted in FIG. 1 for enclosure 156 is on the order of about 24 cm or less and a width of about 13 cm or less and with a thickness of less than 5 cm. Moreover, the anvil configurations provide for an ergonomic instrument with substantially fewer exposed parts, a provision important for handheld instruments. Overall weight is also correspondingly reduced to less than 1.6 kg based on the compactness of the design.

It is noted throughout the present application that the anvil arm 191 configurations, such as that shown in FIG. 3A and FIG. 3B more often include coupled motor driven "force" mechanisms, as directed by configured software, to translate anvil arm 191 so as to provide the intimate contact between surface face 122a of ATR prism 122 and potentially dangerous sample 190 material.

Figure 4A:
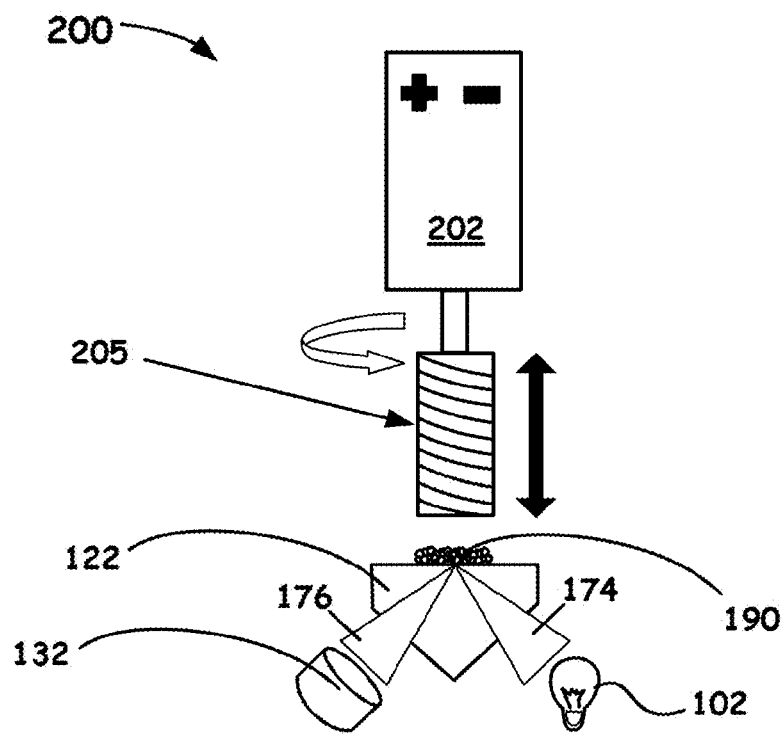
FIG. 4A shows an example general illustration of a "force" mechanism that can translate an ATR anvil arm.
Figure 4B:
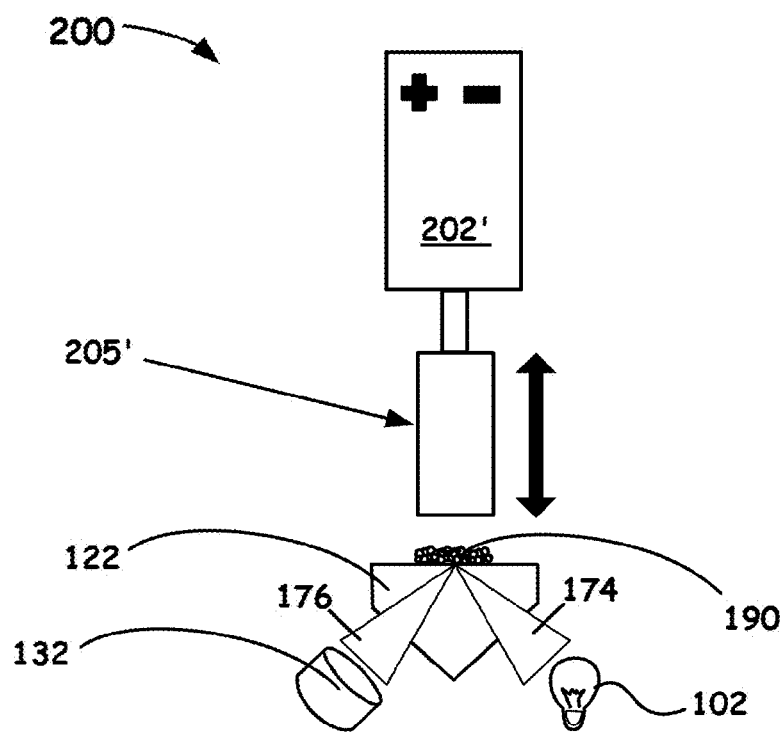
FIG. 4B shows a second example general illustration of a "force" mechanism that can translate an ATR anvil arm.

FIG. 4A and FIG. 4B are example general illustrations of such "force" mechanisms that can be coupled to anvil arm 191 of FIG. 1, FIG. 3A and FIG. 3B. All reference numbers shown in FIG. 4A and FIG. 4B that pertain to the general depiction of ATR prism 122, sample 190, modulated infrared beam 174 and reflected beam 176, source 102, and detector 132 are also similarly referenced with respect to instrument 100, as shown in FIG. 1. FIG. 4A thus shows a non-limiting motor-based force mechanism, generally designated by the reference numeral 200, that uses a rotary motor 202 to cause a screw mechanism 205 to translate (as denoted by double arrows) anvil arm 191 toward sample 190 material in order to apply a controlled force. Such an arrangement can, if configured to do so, exclude the screw mechanism 205 and use a cam (not shown) or other mechanism, as known to those of ordinary skill in the art. A linear motor (not shown) is also an optional embodiment. FIG. 4B shows an alternative non-limiting motor based force mechanism 200, wherein an electromagnet 202' is utilized to translate (again as denoted by double arrows) a rod 205' toward the sample 190 to apply a controlled force. This can be a direct translation or through a mechanism that multiplies the force. It is to be noted however, that while the force mechanisms shown in FIG. 4A and FIG. 4B are beneficial, alternative force mechanisms (actuators) as stated above, can also be utilized. Examples already discussed include DC motors or a solenoid (push solenoid) or any type of force actuator (e.g., piezo-electric driven mechanism, pneumatic or hydraulic actuators, etc.) that can be moved in a controlled manner to provide known or desired controlled compressive forces. Such actuators can also include cam or scissor jack configurations, or even a 4 bar, and if configured as a solenoid, such a solenoid can be, for example, a rotary solenoid that drives a pressure mechanism. The applied contact force using such actuators, while possibly being a fixed force or even a user-selectable force, more often can also be automatically controlled through feedback from the spectrometer based on the spectrometer signature of the sample.

Scan Delay Feature

In certain instances, such as when interrogating dangerous suspect samples with instrument 100, it may be necessary or otherwise desirable to delay commencement of the compression of such materials for a period of time, e.g., via translating anvil arm 191 (as shown in FIG. 1, FIG. 3A and FIG. 3B) downward when wanting to provide intimate contact of sample 190 material with ATR prism 122. Therefore, another example embodiment includes the introduction of a delay between starting the translational movement of anvil arm 191 to enable time to exit the immediate area before the start of measuring any unknown or suspicious materials with instrument 100, as shown by example configurations in FIG. 1, FIG. 3A and FIG. 3B. Accordingly, embodiments disclosed herein may comprise a programmable timer often having a fixed but more often a user pre-set time delay (e.g., about 15 seconds or longer) configured for controlling the timing of the start of the translation of anvil arm 191. Preferably, the timer is electronically controlled by software although a mechanical timer also via software control may be used as an alternative. The timer may also be canceled in response to, for example, non-detected signals. To reiterate, as discussed above, the user presents a sample to the instrument and sets a countdown timer. While the timer is counting down, the user can get to a remote position, after which time the instrument 100 can begin the interrogation of the sample material 190. Once the scan is over, the user can approach the instrument and view the results.

Figure 5:
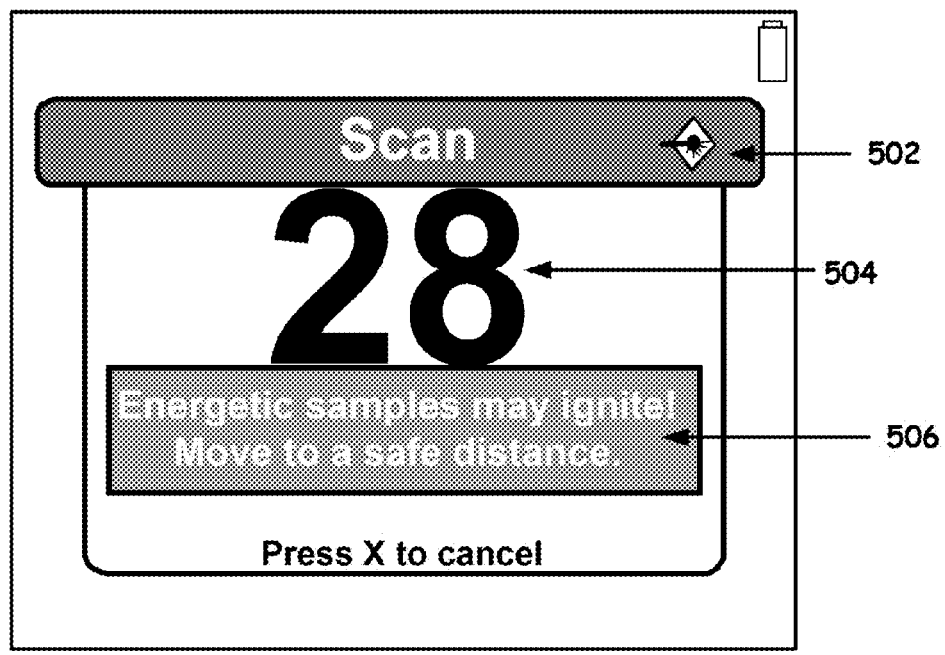
FIG. 5 shows an example graphical user interface (GUI) display of a scan delay (e.g., timed delay interval) function provided herein.

As a more detailed yet still non-limiting operational example, a user often initially raises the anvil arm 191 disclosed herein, and thereafter presses a "scan button" 502, as shown by the example display (i.e., FIG. 5) on instrument 100. However, while the "scan button" 502, shown as a graphic in FIG. 5, can be provided by a touch-screen on instrument 100 (e.g., screen 136 as shown in FIG. 3B), it is also to be appreciated that the scan button function can also be provided by a physical button (not shown) on the instrument 100. Instrument 100, via a graphical user interface (GUI) (not shown) on display 136, as shown in FIG. 3A and FIG. 3B, thereafter provides instructions to user to clean the ATR surface face 122a and a sample contact surface of anvil arm 191. After cleaning the ATR surface face 122a and the sample contact surface of anvil arm 191, the user presses a "continue" button (not shown). The instrument 100 scans the ATR prism 122 to collect a background spectrum. Instrument 100 raises anvil arm 191 (if lowered) and anvil arm 191 moves from a cleaning position to a sample position (i.e., over sample platform 186), as shown in FIG. 3B. Instrument 100 via the GUI instructs user to place sample 190 material on the ATR surface platform 186. The user then selects a scan delay time 504 (e.g., 28 seconds), as shown in FIG. 5. The user presses "scan button" 502 once again wherein the timed countdown (504) begins with a warning 506 for the user to move to a prescribed safe distance. While the timer is counting down, the user exits the immediate area. After the scan time delay selected is reached, the instrument 100 lowers anvil 191 until a particular contact pressure (e.g., an electrical setting is met) is met. If contact pressure is met, instrument 100 begins the infra-red (e.g., FTIR) interrogation of the sample and collects a spectrum. The instrument 100 then raises anvil arm 191 upon completion of the scan. User then safely approaches the instrument to view the result of the one or more scans.

Method(s) for Controlling Applied Force

Figure 6:
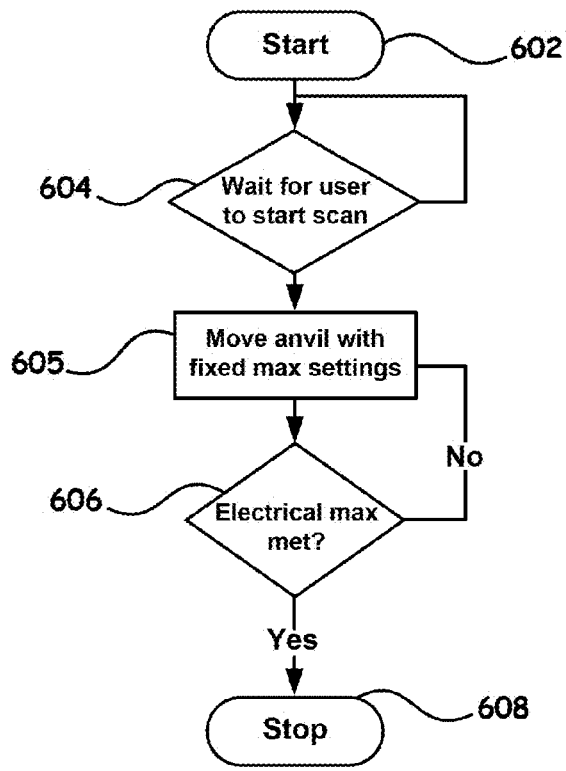
FIG. 6 shows an example flow chart method of a single setting to control the applied contact force.

Various means are capable of being implemented by the embodiments herein to control the force applied to sample materials. The simplest design for such a means is to provide the controlled force(s) in an assembly that uses a single setting for the applied contact force, as generally shown by the flow chart of FIG. 6. Basically, as shown in FIG. 6, the user starts 602 the instrument via the GUI, as discussed above. The instrument then waits for the user to initiate 604 a scan. The anvil arm 191 shown in FIG. 1, FIG. 3A or FIG. 3B then moves 605 after a timed delay (if scan delay option is selected), as also discussed above. The anvil arm 191 moves until it stops 608 based on a user-chosen fixed force that corresponds to an electrical maximum signal 606 within instrument 100 being met. In particular, this method always applies the same force to a sample material.

Figure 7:
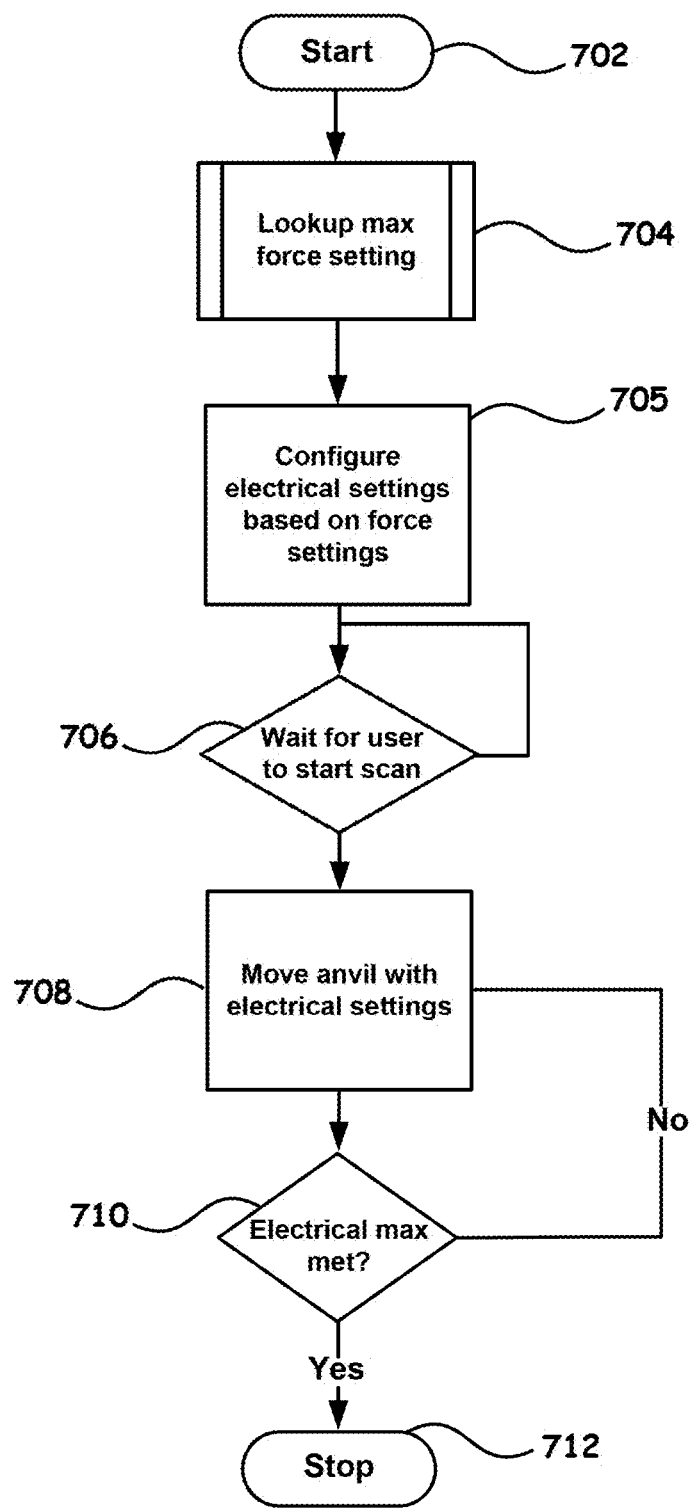
FIG. 7 shows an example flow chart method of the implementation of a programmable discrete setting or predefined use case to control the applied contact force.

An alternative design is to have the force programmable with a user defined setting, as generally described in the flowchart of FIG. 7. Thus, as shown in FIG. 7, the user starts 702 the instrument via the GUI, as discussed above. The user is provided with a lookup table 704 for predefined max force settings based on a particular material or situation. Upon selection, electrical settings based on desired force settings are configured 705 within instrument 100, as shown in FIG. 1. The instrument then waits for the user to initiate 706 a scan. The anvil arm 191 shown in FIG. 1, FIG. 3A or FIG. 3B then moves 708 after timed delay (if scan delay option is selected) based on electrical settings. The anvil arm 191 keeps moving and stops 712 with a programmed force that corresponds to an electrical maximum signal 710. Such a design thus allows the user to select the force through a discrete setting or by selecting a predefined use case. In such a mode of operation, instrument 100, uses the predefined setting for each time the anvil arm 191 is moved.

Figure 8:
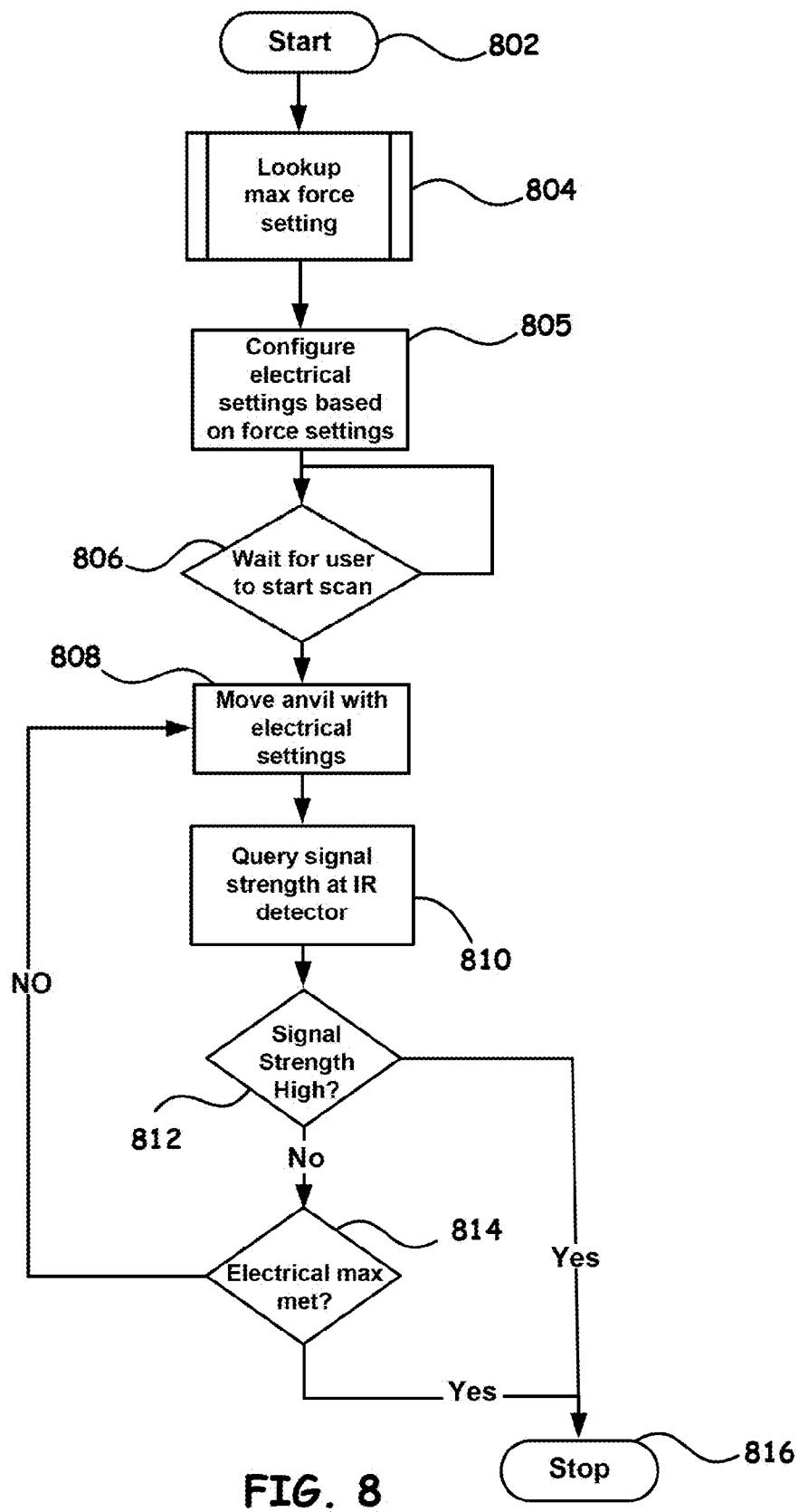
FIG. 8 shows an example flow chart method of controlling the applied contact force by way of sensor feedback provided at the detection end of the optical beam path.

In a more complex design, the movement of anvil arm 191 is configured to be controlled by a sensor (e.g., detector 132, as shown in FIG. 1) at the detection end of the optical beam path. Such a mode of operation is generally shown by the flow chart of FIG. 8. Thus, as shown in FIG. 8, the user starts 802 the instrument via the GUI, as discussed above. The user is provided with a lookup table 804 for predefined max force settings based on a particular material or situation. Upon selection, electrical settings based on desired force settings are configured 805 within instrument 100, as shown in FIG. 1. The instrument then waits for the user to initiate 806 a scan. The anvil 191 shown in FIG. 1, FIG. 3A or FIG. 3B then moves 808 after timed delay (if scan delay option is selected), as discussed above. The anvil 191 keeps moving based on electrical settings 808 while instrument 100 is simultaneously and continuously querying 810 the signal strength provided by Infrared (IR) detector 132 of FIG. 1. If the signal strength (i.e., sample spectroscopic signature strength) provides a reasonable signal, the anvil stops 816. If not, the anvil force is continued and the anvil arm 191 only stops moving 816 when an electrical maximum signal 814 (i.e., desired force as provided by the lookup tables 804) is met or the signal strength (i.e., spectroscopic signature strength) as feedback provided by the sensor 812, is acceptable by instrument 100. This mode of operation enables the anvil arm 191 to stop moving as soon as there is enough contact pressure for a reasonable signal. This is noted to be optimized for pressure sensitive materials where the user desires to want to apply only enough pressure to get a reading.

Another embodiment of the method of FIG. 8 can include taking an initial scan before anvil arm 191 applies force to a sample 190 material. In this configuration, if there is sufficient signal, instrument 100 can be programmed to complete the sample identification without using the anvil arm 191 to apply additional force.

Other variations of the method for controlling the applied force may be via a load cell to measure the force on the ATR as the input to the control loop. Part of the loop may determine that the anvil arm 191 is at maximum force and the signal strength is low. In such a situation, instrument 100 may raise the anvil arm 191 and try bringing the anvil arm 191 back down in an attempt to move the sample enough to reseat it over the ATR with enough contact force. Another non-limiting variation is to stop the scan if the anvil arm 191 is at maximum force and the signal is still too low. After stopping, the instrument 100 can notify the user of the fault with a visual or audible alert.

The preceding discussion has focused on the use of FTIR absorption information to identify a sample. In some embodiments, sample information in addition to infrared absorption information can be used to identify the sample. For example, instrument 100 can be configured to cooperate with other scanning systems to identify samples of interest. Suitable other scanning systems can include, for example, handheld and non-handheld Raman scanning systems. To identify a sample, the sample can first be scanned with a Raman scanning system that is configured to determine an identity of the sample based on Raman scattering information about the sample. The identity determined by the Raman scanning system is then transmitted to instrument 100 and received via communication interface 142, as shown in FIG. 1.

Instrument 100 can also be configured as a single handheld device to also separately determine an identity of the sample based on Raman scattering, as similarly disclosed in U.S. Pat. No. 7,928,391, the disclosure of which is hereby incorporated by reference in its entirety. Thus, if the identities determined via FTIR information and Raman scattering information agree, instrument 100 may also report a successful identification to a system operator. If the identities do not agree, measurement device 100 may report a failed identification. More generally, both the Raman scanning system and instrument 100 can be configured to determine an identity of the sample, and a numerical score or metric that is related to an extent of correspondence between the measured sample information and reference information for the sample. Instrument 100 can then determine, based on the identities reported and the values of the metrics, whether the identification process was successful or not, and to what extent the reported identity of the sample is trustworthy.

The discussion included in this application is intended to serve as a basic description. Although the present invention has been described in accordance with the various embodiments shown and described, one of ordinary skill in the art will readily recognize that there could be variations to the embodiments and those variations would be within the spirit and scope of the present invention. The reader should be aware that the specific discussion may not explicitly describe all embodiments possible; many alternatives are implicit. Such modifications and the like are considered simple modifications that are well within the ability of one of ordinary skill in the art and within the scope and spirit of the invention. Accordingly, many such modifications may be made by one of ordinary skill in the art without departing from the spirit, scope and essence of the invention. Neither the description, drawings nor the terminology is intended to limit the scope of the invention—the invention is defined by the claims.

We claim:

1. A handheld internal reflection apparatus, comprising:
   a handheld enclosure;
   an internally reflective element disposed in the handheld enclosure and also configured to provide a sample contact surface external to the handheld enclosure;
   an optical assembly contained within the handheld enclosure, the optical assembly further comprising a radiation source and a radiation detector, the source being configured to direct radiation towards the sample contact surface and the detector being configured to detect the source radiation optically interacting with the sample contact surface;
   a sample contact arm;
   a motorized force actuator coupled to the sample contact arm; and
   a processor also configured within the handheld enclosure and electronically coupled to the motorized force actuator, the radiation source, and the radiation detector; wherein the processor directs the motorized force actuator with a controlled contact force as applied to a sample disposed between the sample contact arm and the sample contact surface, wherein after the controlled contact force is met, the electronic processor analyzes the sample information received by the radiation detector, and the controlled contact force is configured by the processor as an automatically controlled force based on a feedback spectroscopic signature received by the detector.

2. The handheld internal reflection apparatus of claim 1, wherein the processor is further configured to begin operation of the instrument after a time delay interval.

3. The handheld internal reflection apparatus of claim 1, wherein the processor controlled contact force is a fixed force.

4. The handheld internal reflection apparatus of claim 1, wherein the processor controlled contact force is a user-selectable force.

5. The handheld internal reflection apparatus of claim 1, wherein the sample contact arm is further configured to be manually operated.

6. The handheld internal reflection apparatus of claim 1, wherein the handheld enclosure is configured with a recessed area to enable the sample contact arm to reside and minimize protrusions of the handheld internal reflection apparatus.

7. A handheld internal reflection method, comprising:
   moving a sample contact arm configured with an ATR handheld instrument to a desired position over a sample;
   axially moving the sample contact arm using a processor controlled motorized force actuator, wherein the sample contact arm movement provides an automatically controlled contact force to be applied to the sample and a measuring surface of an internally reflective element based on a feedback spectroscopic signature received by a detector; and
   stopping movement of the sample contact arm after the controlled contact force with the sample and the measuring surface of the internally reflective element meets predefined force settings configured within the ATR handheld instrument.

8. The method of claim 7, further comprising: providing a time delay interval to enable a user to safely move from away the immediate area before axially moving the sample contact arm to enable measurement of the sample.

9. The method of claim 8, further comprising: displaying a message to the user to exit the immediate area after setting the time delay interval.

10. The method of claim 7, further comprising: providing a lookup table that correlates to maximum contact forces of samples selected from energetic and pressure sensitive materials.

11. The method of claim 10, further comprising: moving the sample arm by way of a configured electrical setting based on the lookup table, wherein the configured electrical setting provides a controlled contact force with the sample and the measuring surface of the internally reflective element that is up to the maximum contact force.

12. The method of claim 7, further comprising: moving the sample arm to provide a configured fixed force to the sample and the internally reflective element.

13. The method of claim 7, further comprising: moving the sample arm to provide a user selectable force to the sample and the internally reflective element based on input.

14. The method of claim 7, further comprising: taking an initial scan before the sample contact arm applies force to the sample, wherein if a signal meets a predetermined level, the measurement can be completed without using the sample contact arm to apply additional force.

15. The method of claim 7, further comprising: removing pressure from the sample in a timed operation while the operator is in a remote location.

16. A handheld internal reflection method comprising:
   moving a sample contact arm configured with an ATR handheld instrument to a desired position over a sample;
   axially moving the sample contact arm using a processor controlled motorized force actuator, wherein the sample contact arm movement provides a controlled contact force to be applied to the sample and a measuring surface of an internally reflective element;
   stopping movement of the sample contact arm after the controlled contact force with the sample and the measuring surface of the internally reflective element meets predefined force settings configured within the ATR handheld instrument or provides a reasonable feedback spectroscopic signal of the sample material;
   controlling the applied force via a load cell to measure the force on the ATR via a load cell as the input to a control loop;

axially raising the sample contact arm if the processor detects a predetermined maximum force and a low sample signal; and axially bringing the sample contact arm back into contact with the sample so as to reseat it with a desired contact force.

17. The method of claim 16, further comprising: stopping a scan if the sample contact arm is at maximum force and the signal is still too low, wherein after stopping, the instrument can notify the user of the fault with a visual or audible alert.

* * * * *